US00PP09586P

United States Patent [19]

Fuess

[11] Patent Number: Plant 9,586

[45] Date of Patent: Jun. 18, 1996

[54] CHRYSANTHEMUM NAMED 'EMPIRE DIABLO'

[76] Inventor: Janet S. Fuess, 22 Country Club Dr., New York Mills, N.Y. 13417

[21] Appl. No.: 439,140

[22] Filed: May 11, 1995

[51] Int. Cl.[6] ..... A01H 5/00

[52] U.S. Cl. ..... Plt./82

[58] Field of Search ..... Plt./76, 82

*Primary Examiner*—Howard J. Locker

*Attorney, Agent, or Firm*—Foley & Lardner

[57] ABSTRACT

A new and distinct cultivar of Chrysanthemum plant named Empire Diablo, characterized particular by its red ray florets; almost fully double flower which are very resistant to shattering; compact, cushion habit; 5.0–5.5 cm capitulum diameter; a natural season flower date of September 16; and seven week flower response in light/shade programs.

1 Drawing Sheet

The present invention comprises a new and distinct cultivar of Chrysanthemum, botanically known as *Dendranthema grandiflora,* and hereinafter referred to by the cultivar name Empire Diablo.

Empire Diablo is a product of a planned breeding program which had the objective of creating new chrysanthemum cultivars with freely branching, compact cushion habit, early flower response, rich red decorative flowers, and adaptability for production as a garden variety as well as in a controlled environment. Such traits in combination were not present or needed improvement in previously available commercial cultivars.

Empire Diablo was originated from a hybridization made by the inventor Janet S. Fuess in a controlled breeding program in New Hartford, N.Y. in 1990. The female parent was Empire Cheyenne, an orange-bronze decorative disclosed in U.S. Plant Pat. No. 8,973. The male parent of Empire Diablo was a dark red decorative identified as H87–23, a proprietary breeding line.

Empire Diablo was discovered and selected as one flowering plant within the progeny of the stated parentage by the inventor in Aug. 1991 in a controlled environment in New Hartford, N.Y.

The first act of asexal reproduction of Empire Diablo was accomplished when vegetative cuttings were taken by applicant from the initial selection in Oct. 1991 in a controlled environment in New Hartford, N.Y. Horticultural examination of selected units initiated in Aug. 1992 has demonstrated that the combination of characteristics as herein disclosed for Empire Diablo are firmly fixed and are retained through successive generations of asexual reproduction.

Empire Diablo has not been observed under all possible environmental conditions. The phenotype may vary significantly with variations in environment such as temperature, light intensity, and daylength, without, however, any variation in genotype. The following observations, measurements, and comparisons describe plants grown in New Hartford, N.Y. under natural outdoor conditions which approximate those generally used in commercial practice.

The following traits have been repeatedly observed and are determined to be basic characteristics of Empire Diablo, which in combination distinguish this Chrysanthemum as a new and distinct cultivar:

1. Red ray florets each of which is approximately 2.7 cm long and 0.7 cm wide.
2. Almost fully double flowers—only 18 disc florets present.
3. Flowers are very resistant to shattering.
4. Average of 220 ray florets and 18 disc florets per flower.
5. Capitulum diameter of 5.0–5.5 cm.
6. Seven week flower response in light/shade programs.

7. A natural season flower date of September 16.
8. Compact, cushion habit, making it suitable for production in 4" to 8" containers.

Of the many commercial cultivars known to the present inventor, the most similar in comparison to Empire Diablo is Bravo, disclosed in U.S. Plant Pat. No. 6,888. In comparison to Bravo, Empire Diablo has better color retention, flowers approximately one week earlier in natural season, and has a larger capitulum diameter. The seven week flowering response in light/shade programs, intense red flower color, and compact habit are similar to those same characteristics of Bravo.

The accompanying color photographic drawing shows typical flower and foliage characteristics of Empire Diablo, with colors being as nearly true as possible with illustrations of this type.

In the following description, color references are made to The Royal Horticultural Society Colour Chart. The color values were determined between 10.00 a.m. and 1:00 p.m. on Sep. 8, 1994 under 4,000 footcandles at New Hartford, N.Y.

Classification:

*Botanical.*—*Dendranthema grandiflors* cv. Empire Diablo.

*Commercial.*—Formal decorative garden mum.

INFLORESCENCE

Captiulum:

*Form.*—Decorative.

*Type.*—Almost fully double.

*Diameter across face.*—5.0–5.5 cm.

Corolla of ray florets:

*Color (general tonality from a distance of three meters).*—Intense red.

*Color (upper surface).*—46A.

*Color (under surface).*—45C.

Corolla of disc florets:

*Color (mature).*—7A.

*Color (immature).*—5A.

Reproductive organs:

*Androecium.*—Present on disc florets only; scant pollen.

*Gynoecium.*—Present on both ray and disc florets. Ray: Style 0.6 cm, bifurcated. Disc: Style 0.3 cm, bifurcated, enclosed in anther ring.

PLANT

General Appearance:

*Height.*—24–28 cm, when grown in 8" pot.

Foliage:

*Color (upper surface).*—137B.

*Color (under surface).*—139B.

*Size and shape.*—5.0–6.5 cm long, 4.0 cm wide, 5-lobed.

It is claimed:

1. A new and distinct cultivar of Chrysanthemum plant named Empire Diablo, as illustrated and described.

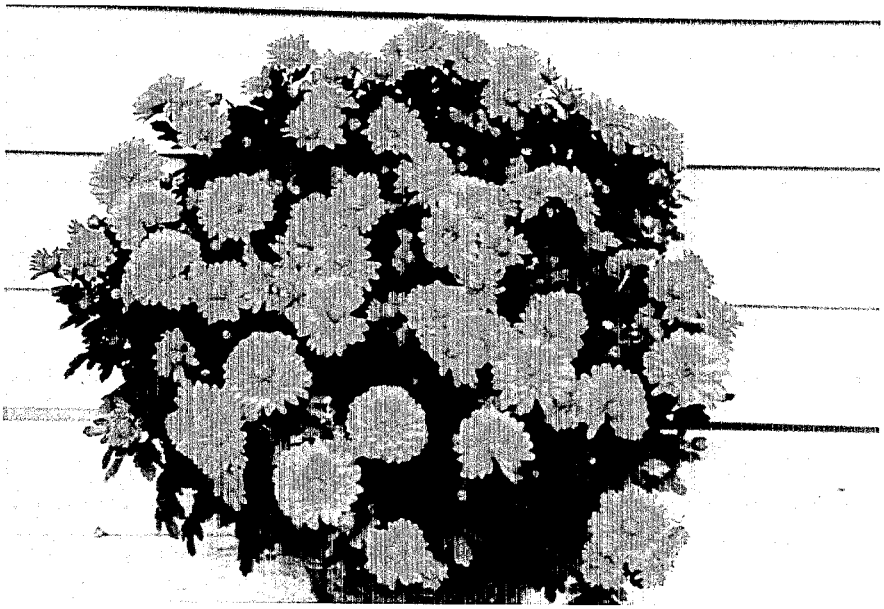

* * * * *